United States Patent [19]

Spivack et al.

[11] 4,093,588
[45] June 6, 1978

[54] HINDERED PHENOLIC CYCLIC PHOSPHONATES AND STABILIZED COMPOSITIONS

[75] Inventors: John D. Spivack, Spring Valley; Martin Dexter, Briarcliff Manor, both of N.Y.

[73] Assignee: Ciba-Geigy Corporation, Ardsley, N.Y.

[21] Appl. No.: 720,304

[22] Filed: Sep. 3, 1976

Related U.S. Application Data

[63] Continuation-in-part of Ser. No. 512,373, Oct. 7, 1974, abandoned, which is a continuation-in-part of Ser. No. 421,173, Dec. 3, 1973, abandoned.

[51] Int. Cl.² .......................... C08K 5/53; C07F 9/15
[52] U.S. Cl. ..................... 260/45.8 R; 260/927 R; 260/937
[58] Field of Search ............. 260/45.8 R, 927 R, 937

[56] References Cited

U.S. PATENT DOCUMENTS

| B 512,373 | 2/1976 | Spivack et al. | 260/937 |
|---|---|---|---|
| 3,787,540 | 1/1974 | Schmidt et al. | 260/970 |
| 3,790,648 | 2/1974 | Schmidt et al. | 260/970 |
| 3,839,506 | 10/1974 | Hechenbleikner et al. | 260/927 R |
| 3,962,377 | 6/1976 | Spivack | 260/937 |

FOREIGN PATENT DOCUMENTS

| 2,455,700 | 6/1975 | Germany | 260/927 R |

*Primary Examiner*—Anton H. Sutto
*Attorney, Agent, or Firm*—Luther A. R. Hall

[57] ABSTRACT

The compounds are hindered phenolic mono- and bicyclic phosphonate compounds having the formula

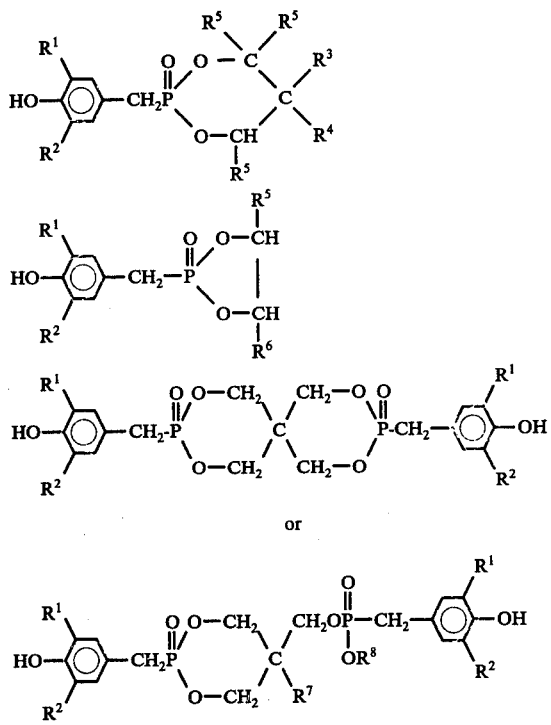

wherein $R^1$ is alkyl, $R^2$ is tert-alkyl, $R^3$ and $R^4$ are independently hydrogen or alkyl, $R^5$ is hydrogen, alkyl or phenyl, $R^6$ is alkyl or phenyl, $R^7$ is lower alkyl and $R^8$ is alkyl, phenyl or phenyl substituted with a lower alkyl group.

These compounds are usually prepared by reaction of a tert-alkylsubstituted hydroxybenzylphosphonate ester with a suitable 1,2 or 1,3 polyol. Alternatively the compounds can be made by reaction of an alkali metal salt of the substituted benzylphosphonic acid with an appropriate alkylene dihalide.

The compounds are useful as stabilizers for organic materials subject to oxidative, thermal or photochemical degradation.

10 Claims, No Drawings

HINDERED PHENOLIC CYCLIC PHOSPHONATES AND STABILIZED COMPOSITIONS

This application is a continuation-in-part of copending application Ser. No. 512,373, filed Oct. 7, 1974, which in turn is a continuation-in-part of Ser. No. 421,173, filed Dec. 3, 1973, both now abandoned.

DETAILED DISCLOSURE

This invention deals with hindered phenolic mono- and bicyclic phosphonate compounds and compositions of organic materials subject to oxidative deterioration stabilized by incorporating therein said compounds.

The phosphonate compounds of this invention can be represented by the formulas

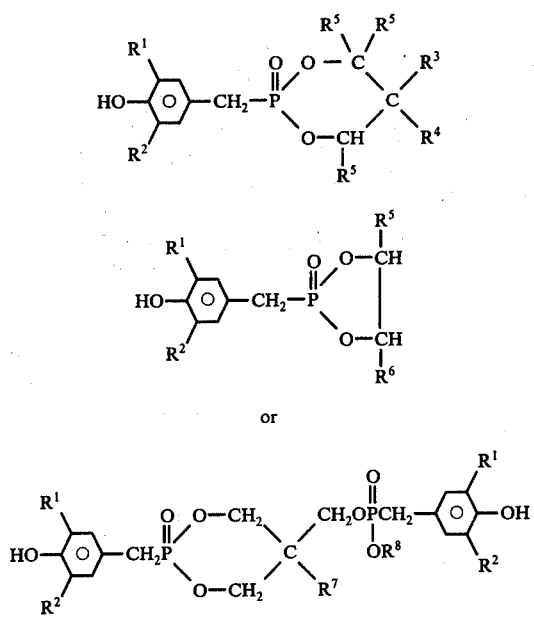

or

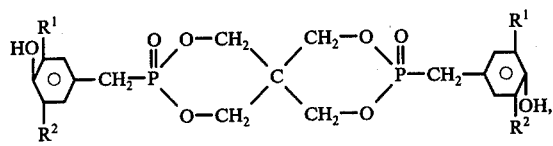

wherein
$R^1$ is alkyl of 1 to 8 carbon atoms,
$R^2$ is tert-alkyl of 4 to 8 carbon atoms,
$R^3$ and $R^4$ are independently hydrogen or alkyl of 1 to 12 carbons, or when $R^5$ is hydrogen, $R^3$ and $R^4$ together may represent the group having the formula

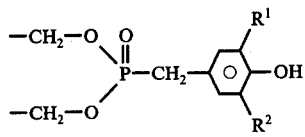

so that this class of compounds has the formula

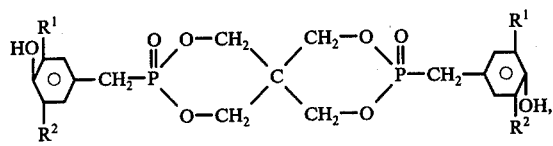

$R^5$ is hydrogen, alkyl of 1 to 8 carbon atoms or phenyl, and providing that each $R^5$ does not have to be the same, $R^6$ is alkyl of 1 to 8 carbon atoms or phenyl, or $R^5$ and $R^6$ together represent tetramethylene, $R^7$ is lower alkyl of 1 to 4 carbon atoms, and
$R^8$ is alkyl of 1 to 8 carbon atoms, phenyl or phenyl substituted with a lower alkyl group of 1 to 4 carbon atoms.

$R^1$ is alkyl of 1 to 8 carbon atoms such as methyl, isopropyl, tert-butyl, tert-amyl and tert-octyl. Preferably $R^1$ is methyl or tert-butyl and most preferably $R^1$ is tert-butyl.

Although $R^2$ can be any tert-alkyl group of 4 to 8 carbon atoms such as tert-butyl, tert-amyl, tert-hexyl or tert-octyl, from the standpoint of commercial availability of starting materials and ease of preparation, tert-butyl is preferred.

The $R^3$ and $R^4$ groups can be independently hydrogen or any alkyl of 1 to 12 carbon atoms, but hydrogen or lower alkyl of 1 to 4 carbon atoms, such as methyl, ethyl or n-butyl, are preferred, and hydrogen or methyl groups are most preferred.

$R^5$ can be hydrogen, phenyl or an alkyl group of 1 to 8 carbon atoms such as methyl, ethyl, n-butyl and n-octyl. Preferably $R^5$ is hydrogen or lower alkyl of 1 to 4 carbon atoms, and most preferably is hydrogen or methyl. Each $R^5$ does not have to be the same in these compounds.

$R^6$ is phenyl or alkyl of 1 to 8 carbon atoms such as methyl, ethyl, n-butyl and n-octyl. Preferably $R^6$ is lower alkyl of 1 to 4 carbon atoms and most preferably is methyl.

Together $R^5$ and $R^6$ can be tetramethylene thus completing a cyclohexane ring with the carbons to which they are attached to form a compound with the formula

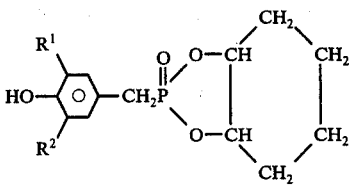

$R^7$ is lower alkyl of 1 to 4 carbon atoms such as methyl, ethyl and n-butyl. Preferably $R^7$ is methyl, ethyl or n-propyl.

$R^8$ is alkyl of 1 to 8 carbon atoms, such as methyl, ethyl, n-butyl or n-octyl, phenyl or phenyl substituted with a lower alkyl group of 1 to 4 carbon atoms such as methyl, ethyl or t-butyl. Preferably $R^8$ is phenyl, tolyl, or alkyl of 1 to 4 carbon atoms, and most preferably $R^8$ is phenyl.

A general procedure which is conveniently used in preparing the stabilizers of this invention is the reaction of an alkylsubstituted hydroxybenzylphosphonate ester with a suitable 1,2 or 1,3 polyol to yield cyclic phosphonates, optionally in the presence of an alkali metal hydride, hydroxide or alkoxide catalyst. A preferred class of alkylsubstituted hydroxybenzylphosphonate esters are the diaryl alkylsubstituted hydroxybenzylphosphonates, and especially preferred are the diphenyl alkylsubstituted hydroxybenzylphosphonates since the by-product phenol is readily removed from the reaction mixture, and can be recovered and reused. The synthetic procedure (1) is shown in the following equation for example:

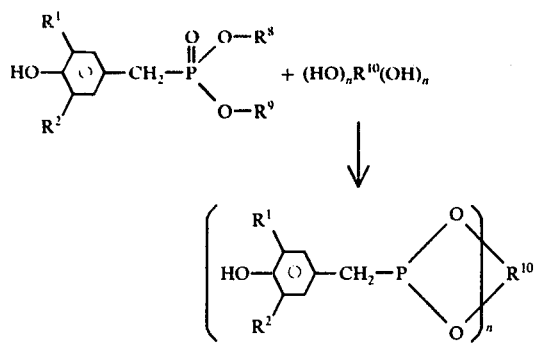

(1)

wherein
R[8] and R[9] are independently alkyl of 1 to 8 carbon atoms, phenyl or phenyl substituted with a lower alkyl group of 1 to 4 carbon atoms.
n is 1 or 2,
R[10] is a 1, 2 or 1,3 divalent alkylene group derived from a 1,2 or 1,3 glycol of 2 to 27 carbon atoms when n is 1, and R[10] is the neopentanetetrayl group of the formula

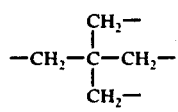

when n is 2.
Where pentaerythritol is used as the 1,3 glycol, and 3,9-dioxo-2,4,8,10-tetraoxa-3,9-diphosphaspiro[5,5]undecane derivative is formed, for example, as follows:

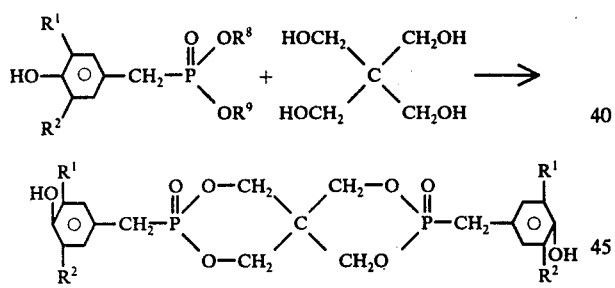

where all symbols are previoiusly defined.

Another general method for preparing the stabilizers of this invention is reacting the alkylsubstituted 4-hydroxybenzylphosphonyl dihalide with the appropriate diol or bis-diol. The method is shown as follows:

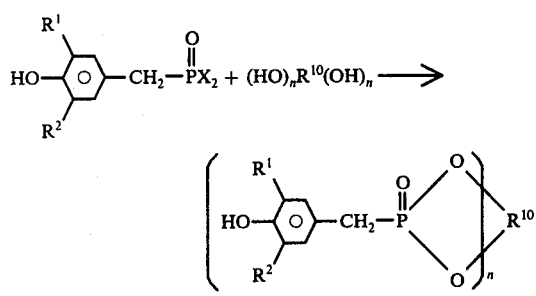

where X is chlorine or bromine.

Stabilizers of the invention can also be made by reacting an alkali metal salt of the O-lower alkyl alkylsubstituted hydroxyphenyl phosphonic acid or the corresponding lower dialkyl ester with the appropriate alkylene dihalide in a solvent as seen in equation (3).

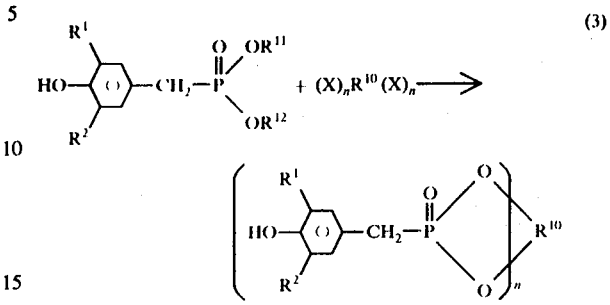

wherein
X is chlorine or bromine,
R[11] is lower alkyl, and
R[12] is lower alkyl or sodium or potassium.

Any solvent that is not reactive with the reactants of this reaction may be employed. Especially useful solvents are dimethylformamide, dimethylacetamide, cyclic sulfones, such as sulfolane, or dimethyl sulfoxide.

Another method consists of reacting a dialkali metal salt of the alkyl-substituted hydroxyphenylphosphonate with appropriate alkylene halide as shown in equation (4).

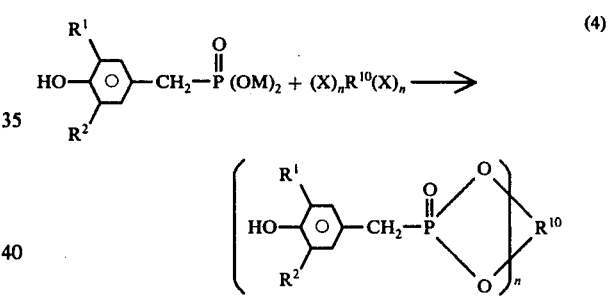

When one mole of a polyol such as 1,1,1-trimethylolethane, 1,1,1-trimethylolpropane or 1,1,1-trimetholylbutane is reacted with two moles of a phosphonate ester

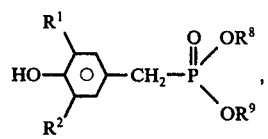

the resulting product is

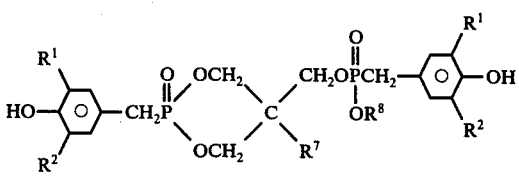

Still other processes for the preparation of phosphonates include the benzylation of a dialkyl phosphite with a benzylated dithiourethane (U.S. Pat. No 3,787,540) or with a benzylamine (U.S. Pat. No.

3,790,648). The preparation of the cyclic ethylene phosphonates by these processes is disclosed.

Illustrative examples of polyols which can be employed in the preparation of the compounds of this invention are given below.

1,2-propanediol
1,3-propanediol
2,2-dimethyl-1,3-propanediol
2,2-diethyl-1,3-propanediol
2-methyl-2-propyl-1,3-propanediol
1,3-butanediol
2,3-butanediol
2-methyl-2,4-pentanediol
1,2-cyclohexanediol
2-ethyl-2-methyl-1,3-propanediol
pentaerythritol
1,1,1-trimethylolethane
1,1,1-trimethylolpropane
1,1,1-trimethylolbutane Following are the illustrative examples of the compounds of this invention:

3,9-bis-(3,5-di-tert-octyl-4-hydroxy-benzyl)-3,9-dioxo-2,4,8,10-tetraoxa-3,9-diphosphaspiro-[5,5]undecane 1-(3,5-di-tert.-butyl-4-hydroxybenzyl)-1-oxo-2,6-dioxa-1-phosphacyclohexane 1-(3,5-di-tert.-amyl-4-hydroxybenzyl)-4,4-diethyl-1-oxo-2,6-dioxa-1-phosphacyclohexane 1-(3,5-di-tert.-octyl-4-hydroxybenzyl)-4-methyl-4-propyl-1-oxo-2,6-dioxa1-phosphacyclohexane 1-(3,5-di-tert.-butyl-4-hydroxybenzyl)-3-methyl-1-oxo-2,6-dioxa-1-phosphacyclohexane 1-(3,5-di-tert.-butyl-4-hydroxybenzyl)-3,4-dimethyl-1-oxo-2,5-dioxa-1-phosphacyclopentane.

1-(3,5-di-tert.-butyl-4-hydroxybenzyl)-3,3,5-trimethyl-1-oxo-2,6-dioxa-1-phosphacyclohexane.

1-(3,5-di-tert.-octyl-4-hydroxybenzyl)-4,4-dimethyl-1-oxo-2,6-dioxa-1-phosphacyclohexane.

1-(3,5-di-tert.-amyl-4-hydroxybenzyl)-4-ethyl-4-methyl-1-oxo-2,6-dioxa-1-phosphacyclohexane.

3,9-bis-(3-methyl-5-tert-butyl-4-hydroxybenzyl)-3,9-dioxo-2,4,8,10-tetraoxa-3,9-diphosphaspiro[5,5]undecane.

1-(3,5-di-tert-butyl-4-hydroxybenzyl)-3-phenyl-1-oxo-2,5-dioxa-1-phosphacyclopentane.

1-(3,5-di-tert.-butyl-4-hydroxybenzyl)-3-methyl-1-oxo-2,5-dioxa-1-phosphacyclopentane.

2-(3,5-di-tert-butyl-4-hydroxybenzyl)-2-oxo-1,3-dioxa-2-phosphahexahydroindane.

Phenyl [1-(3,5-di-tert.-butyl-4-hydroxybenzyl)-4-ethyl-1-oxo-2,6-dioxa-1-phosphacyclohexyl-4]methyl 3,5-di-tert.-butyl-4-hydroxybenzylphosphonate.

The hindered phenolic mono- and bicyclic phosphonates of this invention are stabilizers of organic material normally subject to the thermal and oxidative deterioration. Materials which are thus stabilised include synthetic organic polymeric substances such as vinyl formed from the polymerization of vinyl halides or from the copolymerization of vinyl halides with unsaturated polymerizable compounds, e.g., vinyl esters, $\alpha,\beta$-unsaturated ketones, $\alpha,\beta$ unsaturated aldehydes and unsaturated hydrocarbons such as butadienes and styrene; polyolefins such as polyethylene, polypropylene, polybutylene including copolymers of $\alpha$-olefins such as ethylene/propylene copolymer; dienes such as polybutadiene, polyisoprene, and the like, including copolymers with other monomers; polyurethanes and polyamides such as polyhexamethylene adipamide and polycaprolactam; polyesters such as polyethylene terephthalates or polybutylene terephthalates; polycarbonates; polyacetal; polystyrene, polyethylene oxide; and copolymers such as those of high impact polystyrene containing copolymers of butadiene and styrene and those formed by the copolymerization of acrylonitrile, butadiene and/or styrene; natural and synthetic rubbers such as ethylene/propylene/diene copolymers (EPDM) and chlorinated rubber; and polyphenylene oxide and copolymers.

Other materials which can be stabilized by the compounds of the present invention include lubricating oil of the aliphatic ester type, i.e., di(2-ethylhexyl) azelate, and other synthetic ester lubricants, pentaerythritol tetracaproate, and the like; animal and vegetable derived oils, e.g., linseed oil, castor oil, palm oil, corn oil, cottonseed oil, and the like; hydrocarbon materials such as gasoline, mineral oil, fuel oil, drying oil, cutting fluids, waxes, resins, and the like, salts of fatty acids such as soaps and the like; and alkylene glycols, e.g., $\beta$-methoxyethylene glycol methoxytriethylene glycol, triethylene glycol, octaethylene glycol, dibutylene glycol, dipropylene glycol and the like.

The compounds of this invention are particularly effective as stabilizers for polyamides (eg. nylon 6 and nylon 66) and for polyesters. The phosphonates of this invention are very effective in preventing the loss of polymer viscosity of polyamides when the polyamides containing said phosphonates are exposed to long heating in air at elevated temperatures.

When used with thiosynergists, the phosphonates of this invention are also effective antioxidants for polyolefins such as polypropylene, polyethylene, ethylene-propylene copolymer and others. When used in combination with UV stabilizers, they are very effective light stabilizers. They are also good polyolefin processing stabilizers where thermal degradation is especially severe.

The substrates of particular importance are olefin polymers such as polyethylene and polypropylene. Polypropylene is especially well stabilized by the compounds of this invention.

In general, the stabilizers of this invention are employed from 0.01 to 5% by weight of the stabilized composition, although this will vary with the particular substrate and application.. As advantageous range is from about 0.05 to about 2% and especially from 0.1 to about 1%.

For addition to polymeric substrates, the stabilizers can be blended before polymerization or after polymerization, during the usual processing operations, for example, by hot-milling, the composition then being extruded, pressed, or the like into films, fibers, filaments, hollow spheres and the like. The heat stabilizing properties of these compounds advantageously stabilize the polymer against degradation during such processing at the high temperature generally encountered.. The stabilizers can also be dissolved in suitable solvents and sprayed on the surface of films, fabrics, filaments or the like to provide effective stabilization.

These compounds can also be used in combination with other additives such as sulfur-containing esters, e.g., distearyl $\beta$-thiodipropionate (DSTDP), dilauryl $\beta$-thiodipropionate (DLTDP), in an amount of from 0.01 to 2% by weight of the organic material, and the like, pourpoint depressants, corrosion and rust inhibitors, dispersing agents, emulsifiers, antifoaming agents, carbon black, accelerators and other chemicals used in rubber compounding, plasticizers, color stabilizers, fillers, surface active agents di- and tri-alkyl- and alkylphenyl-phosphites, heat stabilizers, ultraviolet light stabilizers, antiozonants, dyes, pigments, metal chelating agents, dyesites, and the like.. Often combinations such as these, particularly the sulfur containing esters, the phosphites and/or the ultraviolet light stabilizers will produce superior results in certain applications to those expected by the properties of the individual components.

The followinng formula represents co-stabilizers which are in certain instances very useful in combination with the stabilizers of the invention:

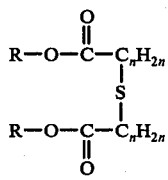

wherein R is an alkyl group having from 6 to 24 carbon atoms; and $n$ is an integer from 1 to 6. Especially useful compounds of this type are dilauryl β-thiodipropionate and distearyl β-thiodipropionate. The above co-stabilizers are used in the amount of from 0.01 to 2% by weight of the organic material, and preferably from 0.1 to 1%.

In addition to the above noted additives that can be employed in combination with the compounds of this invention, it is often especially advantageous to employ also light stabilizers. The light stabilizers are used in the amount of from 0.01 to 5% by weight of the organic material, and preferably from 0.1 to 1%. Illustrative examples of light stabilizers are listed below.

UV absorbers and light protection agents 2-(2'-hydroxyphenyl)-benztriazoles, such as for example, the 5'-methyl-, 3',5'-di-tert.-butyl-, 5'-tert.-butyl-, 5'-(1,1,3,3-tetramethyl-butyl)-, 5-chloro-3', 5'-di-tert.-butyl-, 5-chloro-3'-tert.-butyl-5'-methyl-, 3'-sec.-butyl-5'-tert.-butyl-, 3'-{α-methyl-benzyl}-5'-methyl-, 3'-{α-methylbenzyl}-5'-methyl-5-chloro-, 4'-hydroxy-, 4'-methoxy-, 4'-octoxy-, 3',5'-di-tert.-amyl-, 3'-methyl-5'-carbomethoxyethyl- or 5-chloro-3',5'-di-tert.-amyl- derivatives.

2,4-Bis-(2'-hydroxyphenyl)-6-alkyl-s-triazines, such as, for example, the 6-ethyl-, 6-undecyl- or 6-heptadecyl-derivatives.

2-Hydroxy-benzophenones, such as, for example, the 4-hydroxy-, 4-methoxy-, 4-octoxy-, 4-decyloxy-, 4-dodecyloxy-, 4-benzyloxy-, 4,2',4'-trihydroxy or 2'-hydroxy-4,4'-dimethoxy-derivatives.

1,3-Bis-(2'-hydroxy-benzoyl)-benzenes, such as, for example, 1,3-bis-(2'hydroxy-4'-hexyloxy-benzoyl)-benzene, 1,3-bis-(2'-hydroxy-4'-octoxy-benzoyl)-benzene and 1,3-bis-(2'-hydroxy-4'-dodecyloxy-benzoyl)-benzene.

Esters of optionally substituted benzoic acids, such as, for example, phenyl salicylate, octylphenyl salicylate, di-benzoylresorcinol, bis-(4-tert.-butyl-benzoyl)-resorcinol, benzoyl-resorcinol, 3,5-di-tert.-butyl-4-hydroxybenzoic acid 2,4-di-tert.-butyl-phenyl ester, octadecyl ester or 2-methyl-4,6-di-tert.-butylphenyl ester.

Acrylates, such as, for example, α-cyano-β,β-diphenyl-acrylic acid ethyl ester or isooctyl ester α-carbomethoxy-cinnamic acid methyl ester, α-cyano-β-methyl-p-methoxy-cinnamic acid methyl ester or butyl ester and N-(β-carbomethoxy-vinyl)-2-methyl-indoline.

Nickel compounds, such as, for example, nickel complexes of 2,2-thio-bis-4-(1,1,3,3-tetramethylbutyl)-phenol such as the 1:1 and 1:2 complex, optionally with other ligands such as n-butylamine, triethanolamine or N-cyclohexyl-diethanolamine; nickel complexes of bis-{2-hydroxy-4-(1,1,3,3-tetramethylbutyl)-phenyl}-sulphone, such as the 2:1 complex optionally with other ligands such as 2-ethyl-caproic acid; nickel dibutyldithiocarbamate, nickel salts of 4-hydroxy-3,5-di-tert.-butyl-benzylphosphonic acid monoalkyl esters, such as the methyl, ethyl or butyl ester, the nickel complex of (2-hydroxy-4-methyl-phenyl)undecyl-ketonoxime and nickel 3,5-di-tert.-butyl-4-hydroxybenzoate.

Oxalic acid diamides, such as, for example, 4,4'-dioctyloxyoxanilide, 2,2'-dioctyloxy-5,5'-di-tert.-butyl-oxanilide, 2,2'-di-dodecyloxy-5,5'-di-tert.-butyloxanilide, 2-ethoxy-5-tertiarybutyl-2'-ethyl-oxanilide, 2-ethoxy-2'-ethyl-oxanilide, N,N'-bis(3-dimethylaminopropyl) oxalamide, mixtures of o- and p-methoxy and o- and p-ethoxy-di-substituted oxanilides and mixtures of 2-ethoxy-5-tert.-butyl-2'-ethyl-oxanilide with 2-ethoxy-2'-ethyl-5,4'-di-tert..-butyl-oxanilide.

Sterically hindered amines, such as for example, 4-benzoyloxy-2,2,6,6-tetramethylpiperidine, 4-stearoyloxy-2,2,6,6-tetramethylpiperidine, bis-(2,2,6,6-tetramethylpiperidyl)sebacate and 3-n-octyl-7,7,9,9-tetramethyl-1,3-triaza-spiro-[4,5]decane-2,4-dione.

EXAMPLE 1

3,9-Bis-(3,5-di-tert.-butyl-4-hydroxybenzyl)-3,9-dioxo-2,4,8,10-tetraoxa-3,9-diphosphaspiro[5,5]undecane 27.2 Grams of pentaerythritol, 64 milligrams of lithium hydride and 18.1 grams of diphenyl 3,5-di-tert.-butyl-4-hydroxybenzylphosphonate were melted together and heated in a nitrogen atmosphere at atmosphere pressure at a reaction temperature of 160°–180° for 1½ hours, and at reduced pressure (12 mm Hg) at 155° to 170° C for an additional 4½ hours.

During this latter period of heating at reduced pressure, the evolved phenol of reaction was removed from the reaction mixture by distillation.

The light-colored glass obtained was dissolved in 100 ml of warm benzene and successively washed with water containing a little acetic acid and then with water. After drying over anhydrous sodium sulfate, the drying agent was separated by filtration and the clear filtrate freed of solvent by distillation at reduced pressure. Trituration of the residue with hot ether yielded white crystals melting at 248° to 253° C.

Crystallization from isopropanol yielded white crystals melting at 250° to 252° C. (Compound 1)

When the procedure of the above example is repeated employing diphenyl 3,5-di-tert-octyl-4-hydroxybenzylphosphonate, the resulting compound is 3,9-bis-(3,5-di-tert-octyl-4-hydroxybenzyl)-3,9-dioxo-2,4,8,10-tetraoxa-3,9-diphosphaspiro[5,5]undecane.

EXAMPLE 2

1-(3,5-di-tert.-butyl-4-hydroxybenzyl)-4,4-dimethyl-1-oxo-2,6-dioxa-1-phosphacyclohexane 22.6 Grams of diphenyl 3,5-di-tert.-butyl-4-hydroxybenzylphosphonate, 0.3 grams of sodium methylate and 5.2 grams of 2,2-dimethyl-1,3-propanediol were charged successively under nitrogen and heated at 160° to 180° C for 1 hour at atmospheric pressure, and then at 182° to 198° C at reduced pressures initially at 15 mm Hg, and finally at 2 mm Hg. During the heating at reduced pressure, the evolved phenol was removed by distillation. The glassy residue was crystallized twice from cyclohexane yielding white crystals melting at 136° to 137° C. (Compound 2)

Similarly, 1-(3,5-di-tert-octyl-4-hydroxybenzyl)-1-oxo-2,6-dioxa-1-phosphacyclohexane is made by substituting 1,3-propanediol for 2,2-dimethyl-1,3-propanediol and diphenyl 3,5-di-tert-octyl-4-hydroxybenzylphosphonate for diphenyl 3,5-di-tert-butyl-4-hydroxybenzylphosphonate in the above example.

EXAMPLE 3

1(3,5-di-tert.-butyl-4-hydroxybenzyl)-1-oxo-2,5-dioxa-1-phosphacyclopentane

The compound of this example was made by substantially the same procedure as Example 2 by substituting ethylene glycol for 2,2-dimethyl-1,3-propanediol in Example 2. After crystallization from a solvent mixture of cyclohexanebenzene, the product was obtained as white crystals melting at 166° to 169° C. (Compound 3)

Similarly, 1-(3,5-di-tert-amyl-4-hydroxybenzyl)-3-methyl-1-oxo-2,5-dioxa-1-phosphacyclopentane is made by substituting 1,2-propanediol for 2,2-dimethyl-1,3-propanediol and diphenyl 3,5-di-tert-amyl-4-hydroxybenzylphosphonate for diphenyl 3,5-di-tert-butyl-4-hydroxybenzylphosphonate in Example 2.

EXAMPLE 4

Oven Aging Test

Unstabilized polypropylene powder (Hercules Profax 6501) was thoroughly blended with the stabilizers shown in Table I. The blended material was then milled on a two roller mill at 182° C for 10 minutes after which time the stabilized polypropylene was sheeted from the mill and allowed to cool.

The milled polypropylene sheet was then cut into small pieces and pressed for 7 minutes on a hydraulic press at 218° C and 2000 psi (19.25 Kg/cm$^2$)pressure. The resultant sheet of 25 mil (0.635 mm) thickness was cut into small plaques and tested for resistance to accelerated aging in a tubular oven at 150° C. This oven contains cyclindrical glass tubes laid horizontally in the oven. Air was passed through the tubes at a rate of 400 cu ft (11.33 cubic meters) per minute. When the plaques showed the first signs of decomposition (e.g. cracking or brown edges), they were considered to have failed. The data obtained are reported in Table I below.

TABLE I

| Polypropylene Oven Aging at 150° C | |
|---|---|
| Stabilizer | Hours to Failure |
| 0.25% Compound of 1 + 0.5% UV stabilizer A | 56 |
| 0.1% Compound 1 + 0.3% Dilaurylthiodipropionate | 560 |
| 0.25% Compound 2 + 0.5% UV stabilizer A | < 27 |
| 0.1% Compound 2 + 0.3% Distearylthiodipropionate | 320 |
| 0.25% Compound 2 | < 27 |
| None | 3 |

UV stabilizer A is 2(2-hydroxy-3,5-di-t-butylphenyl)-5-chlorobenzotriazole; it does not affect oven aging of polypropylene significantly.

EXAMPLE 5

Artificial Light Exposure Test

The samples prepared by the procedure described in Example 4 were also tested for light stability. This test was conducted in a FS/BL unit, basically of the American Cyanamid design, which consists of 40 tubes of alternating fluorescent sun lamps and black lights (20 of each). The 25 mil (0.635 mm) plaques were mounted on 3 × 1 inch (7.62 cm × 2.54 cm) IR card holders with ¼ × 1 inch (0.635 cm × 2.54 cm) windows and were placed on a rotating drum 2 inches (5.08 cm) from the bulbs in the FS/BL unit. The time in hours to embrittlement was noted. This was determined when the sample was bent 180° and cracking developed.

The test results in Table II were obtained according to the procedures described above. The amounts of additives are expressed in weight percent based on the weight of the polymer.

TABLE II

| Polypropylene Artificial Light Exposure | |
|---|---|
| Stabilizer | Hours to Embrittlement |
| 0.25% Compound 1 + 0.5% UV stabilizer A | 1200* |
| 0.25% Compound 2 + 0.5% UV stabilizer A | 1500* |
| | 1175 |
| 0.25% Compound 2 | 150 |

*These two results were obtained at different times.

EXAMPLE 6

Nylon 6

50 Grams of caprolactum were mixed with 5% of its weight of aminocaproic acid and 0.5% of its weight of Compound 2, and the mixture was polymerized under high purity flowing nitrogen for 6 hours at 256° C. The polymer was then cooled with dry ice, broken into small pieces with a hammer and ground to 10 mesh in a Wiley mill. The resulting granules were then washed 5 times with preboiled distilled water at 100° C under an atmosphere of flowing nitrogen. The resulting material was dried at 105° C for 24 hours under 0.3 mm Hg vacuum. Gardner Colors were then recorded for the granules.

Initial relative viscosities of 1% sulfuric acid solutions were then determined. The granules were oven-aged in an aluminum weighing dish in a forced-draft oven at 140° C for 65 hours. The viscosities were again determined and reported as percent retention of initial viscosities. Colors were recorded as Gardner colors, before and after oven-aging. Nylon 6 with the Compound 2 stabilizer present degraded less on oven aging as seen by viscosity measurements than did nylon 6 with no stabilizer present.

Gas fume tests were run on granules wrapped in an unstabilized nylon cloth bag by exposing for 20 uninterrupted cycles in an AATCC gas fume chamber. Color changes were visually evaluated.

When Compound 2 was employed as a stabilizer, the color of nylon, both during polymerization and after washing, was white.

All results are shown in Table III.

EXAMPLE 7

Nylon 66

39.3 Grams of nylon 66 salt were mixed with 0.177 grams of hexamethylenediamine diacetate and 0.183 grams of Compound 1. The mixture was polymerized under flowing high purity nitrogen for 1 hour at 180° C., 1 hour at 280° C. and finally one-half hour under vacuum. After cooling, the nylon plug was removed from the glass polymerization tube by breaking the same. The plug was then cooled with dry ice, broken into small pieces with a hammer and ground in a Wiley mill to 10-mesh granules.

The specific viscosities of a 1% sulfuric acid solution were determined initially. The polymer granules were then oven aged in an aluminum weighing dish in a forced draft oven at 140° C for 65 hours. The specific viscosities of a 1% sulfuric acid solution were again determined after this oven aging and the percent of the original specific viscosities determined. Nylon 66 with Compound 1 stabilizer present retained much more of its original viscosity indicating much less degradation than when no stabilizer was present.

Results are shown in Table IV.

TABLE III

Stabilization of Nylon 6 with Compound 2 According to Example 6

|  | Compound 2 | No Stabilizer |
|---|---|---|
| Initial Relative Viscosity After Polymerization of Nylon 6 | 1.83 | 1.84 |
| Percent Retention of Initial Relative Viscosity after 65 Hours of Oven Aging at 140° C. | 84 | 69 |
| Gardner Colors[1] of Polymer Granules After |  |  |
| a) Polymerization | 2 | 1 |
| b) 65 hrs. at 140° C | 6 | 6.5 |
| c) Gas Fumes Test | 4 | 1 |

[1]Gardner color scale is from 1 to 16. The higher the color the more discolored the sample is. The color standards are available from the Gardner Laboratories.

TABLE IV

Stabilization of Nylon 66 with Compound 1 According to Example 7

|  | Specific Viscosity | |
|---|---|---|
| Stabilizer | Initial | % Retention after Oven Aging for 65 Hours at 140° C |
| Compound 1 | 1.15 | 94 |
| None | 1.18 | 65 |

EXAMPLE 8

Stabilization of Polyester

Unstabilized poly(ethylene terephthalate) powder (TERLENKA, Enka) was thoroughly mixed under a nitrogen atmosphere at elevated temperatures with the stabilizers shown on Table V for a 30-minute period. Using the stabilizer of Example 1, the mixing temperature was 275° C while with the stabilizer of Example 2 the mixing temperature was 285° C.

The stabilization efficacy of the cyclic phosphonates was determined by placing a stabilized sample of polyester in a differential scanning calorimeter operated under the following conditions:

| Range | 4 millicalories/second |
|---|---|
| Heating rate | 1° C/minute |
| Chart speed | 5 mm/minute |
| Oxygen stream | ca. 15 ml/minute |

The oxidation temperature (Tox) is taken as the temperature at which the onset of a change in the endotherm takes place. The endotherm is caused by the weight loss due to the evolution of volatile decomposition products such as carbon monoxide, carbon dioxide, acetaldehyde, water and the like.

A blank sample of polyester without stabilizer was run as a control.

TABLE V

Polyester Oxidation Temperature

| Stabilizer | Oxidation Temperature (Tox)° C | Δ Tox, ° C* |
|---|---|---|
| Blank (processed at 275° C) | 247 | — |
| 1% (by weight) Compound 1 in polyester | 291 | +44 |
| Blank (processed at 285° C) | 246 | — |
| 0.1% (by weight) Compound 2 in polyester | 257 | +11 |

* ΔTox indicates the difference in oxidation temperature caused the presence of the cyclic phosphonate stabilizer in the polyester. Both Compounds 1 and 2 were quite effective in raising the temperature before decomposition of the polyester begun.

What is claimed is:

1. A compound having the formula

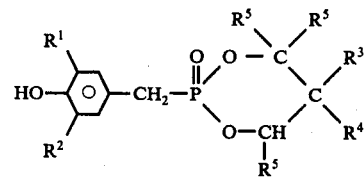

or

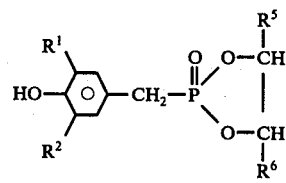

wherein
$R^1$ is alkyl of 1 to 8 carbon atoms,
$R^2$ is tert-alkyl of 4 to 8 carbon atoms,
$R^3$ and $R^4$ are independently hydrogen or alkyl of 1 to 12 carbon atoms,
$R^5$ is hydrogen, alkyl of 1 to 8 carbon atoms or phenyl and providing that each $R^5$ does not have to be the same, and
$R^6$ is alkyl of 1 to 8 carbon atoms or phenyl, or $R^5$ and $R^6$ together represent tetramethylene.

2. A composition of matter comprising a polyamide subject to oxidative and thermal deterioration stabilized with from 0.01 to 5% by weight of a compound of claim 1.

3. A composition according to claim 2 wherein the stabilizing compound is 1-(3,5-di-tert-butyl-4-hydroxybenzyl)-4,4-dimethyl-1-oxo-2,6-dioxa-1-phosphacyclohexane.

4. A compound of claim 1 wherein
$R^1$ is methyl or tert-butyl,
$R^2$ is tert-butyl, $R^3$ and $R^4$ are independently hydrogen or lower alkyl of 1 to 4 carbon atoms,
$R^5$ is hydrogen or lower alkyl of 1 to 4 carbon atoms,
$R^6$ is lower alkyl of 1 to 4 carbon atoms.

5. A compound of claim 1 wherein
$R^1$ is tert-butyl,
$R^2$ is tert-butyl,
$R^3$, $R^4$ and $R^5$ are independently hydrogen or methyl,
$R^6$ is methyl.

6. A compound of claim 1 wherein
$R^1$ and $R^2$ are tert-butyl.

7. A compound of claim 1 wherein
$R^3$ and $R^4$ are independently hydrogen or methyl.

8. A compound of claim 1 wherein
$R^5$ is hydrogen or methyl, and
$R^6$ is methyl.

9. A compound of claim 1 wherein
$R^3$, $R^4$ and $R^5$ are independently hydrogen or methyl, and
$R^6$ is methyl.

10. The compound of claim 1 which is 1-(3,5-di-tert.-butyl-4-hydroxybenzyl)-4,4-dimethyl-1-oxo-2,6-dioxa-1-phosphacyclohexane.

* * * * *